US006186403B1

United States Patent
Ozbey et al.

(10) Patent No.: US 6,186,403 B1
(45) Date of Patent: Feb. 13, 2001

(54) METHOD AND APPARATUS FOR ACCURATE COLOR READING OF MATERIAL HAVING VARIABLE DEPTH AND MOTIF

(76) Inventors: Yalcin Ozbey, 355 Mallard La., Earlysville, VA (US) 22936; Jerry Sharpe, Highway 15 Fork Union, Fork Union, VA (US) 23055; David Hillcoat, 1341 Huntersfield Ct., Keswick, VA (US) 22947

(*) Notice: Under 35 U.S.C. 154(b), the term of this patent shall be extended for 0 days.

(21) Appl. No.: 09/190,847

(22) Filed: Nov. 12, 1998

Related U.S. Application Data

(60) Provisional application No. 60/097,411, filed on Aug. 21, 1998, and provisional application No. 60/065,160, filed on Nov. 12, 1997.

(51) Int. Cl.[7] ................................................ G06K 19/00
(52) U.S. Cl. ..................... 235/487; 235/486; 235/469; 8/400; 356/244
(58) Field of Search .................................. 235/487, 486, 235/469; 8/400; 356/244, 402

(56) References Cited

U.S. PATENT DOCUMENTS

| | | | |
|---|---|---|---|
| 4,682,890 | * 7/1987 | De Macario et al. | 356/244 |
| 4,695,727 | * 9/1987 | Brierley et al. | 250/328 |
| 4,703,943 | * 11/1987 | Zelenko et al. | 281/21 R |
| 5,174,674 | * 12/1992 | Norwood | 402/73 |
| 5,180,062 | * 1/1993 | Stables | 206/574 |
| 5,230,709 | * 7/1993 | Holfeld et al. | 8/400 |
| 5,245,171 | * 9/1993 | Fox et al. | 235/492 |
| 5,303,487 | * 4/1994 | Olson | 40/124.1 |
| 5,318,598 | * 6/1994 | Holfeld et al. | 8/400 |
| 5,366,511 | * 11/1994 | Holfeld et al. | 8/400 |
| 5,506,935 | * 4/1996 | Eppley | 235/486 |
| 5,519,218 | * 5/1996 | Chang | 250/339.07 |
| 5,677,524 | * 10/1997 | Haghiri-Tehrani | 235/492 |
| 5,701,175 | * 12/1997 | Kostizak et al. | 356/326 |

\* cited by examiner

Primary Examiner—Michael G Lee
Assistant Examiner—Diane I. Lee
(74) Attorney, Agent, or Firm—Sheldon H Parker

(57) ABSTRACT

A card, generally rectangular, for maintains a material in a fixed position is dimensioned to interact with the holding plate for use with a spectrophotometer. A pair of polygon windows within the card are aligned with the window of the holding plate which aligns with the window of the spectrophotometer. The card can be sealed to secure itself when folded and retain the material overlaying the window within the folded card. A fabric recess preferable encompasses one of the windows and a fabric adhesive, preferably releasable, maintains the fabric swatch in position. The fabric adhesive can be placed within the fabric recess or encompassing an opposing window. The cards are stored within a pocketed holder having pockets dimensioned to individually store multiple cards on a sheet. The holding plate is dimensioned to be received and affixed to a spectrophotometer. A slot, open at one end of the holding plate, retains the cards. A light interactive material, such as industry approved color tiles, is placed in a recessed receiving area adjacent the window opposite the spectrophotometer. A lip spaced from the back wall, extends around at least a portion of the recessed area perimeter. A portion of the slot is open to the recessed area. A die cutter for consistently aligning and cutting has a hollow base containing a light source and a transparent top panel with marking indices. A resilient cutting base encompasses the transparent top panel.

2 Claims, 13 Drawing Sheets

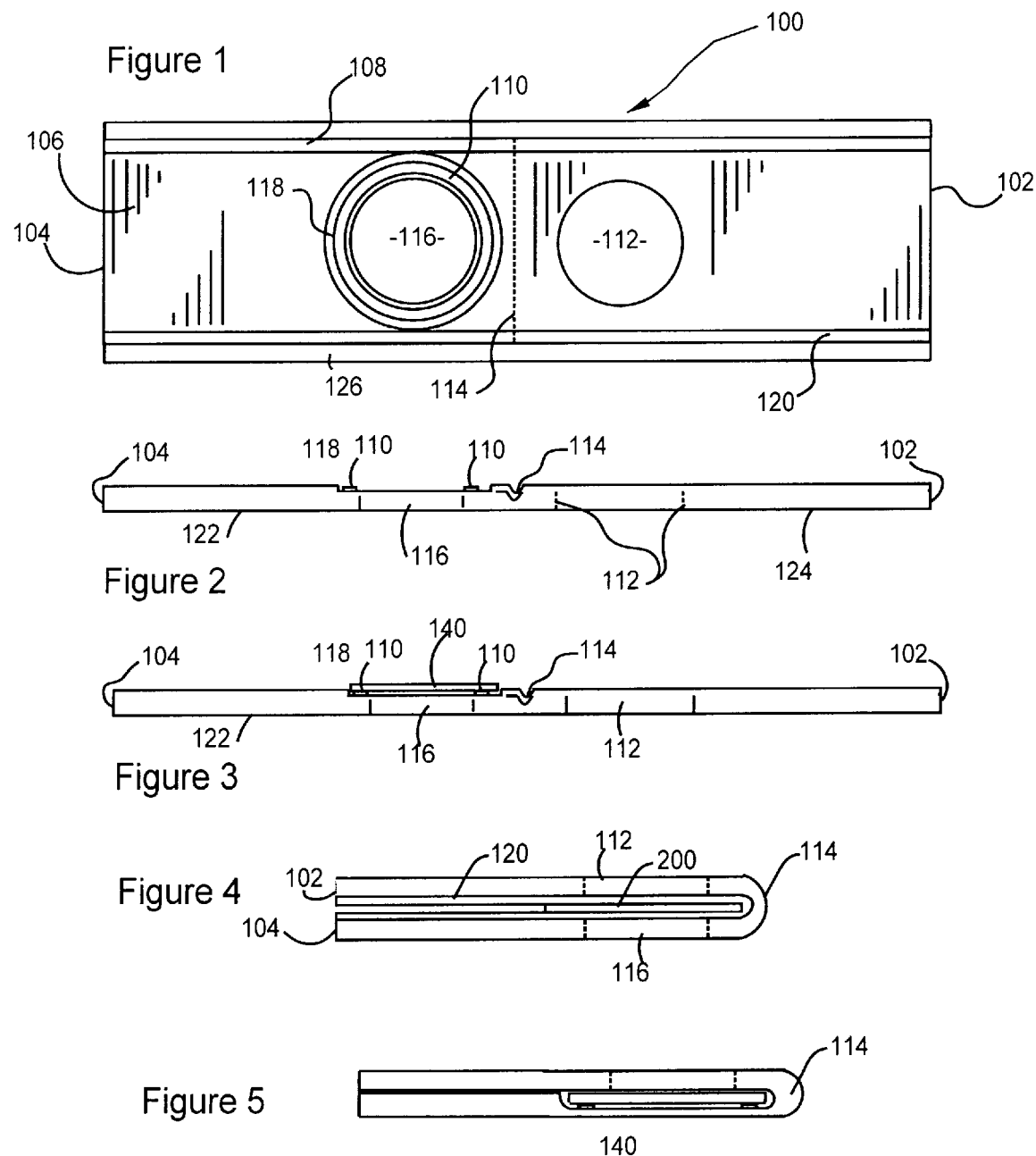

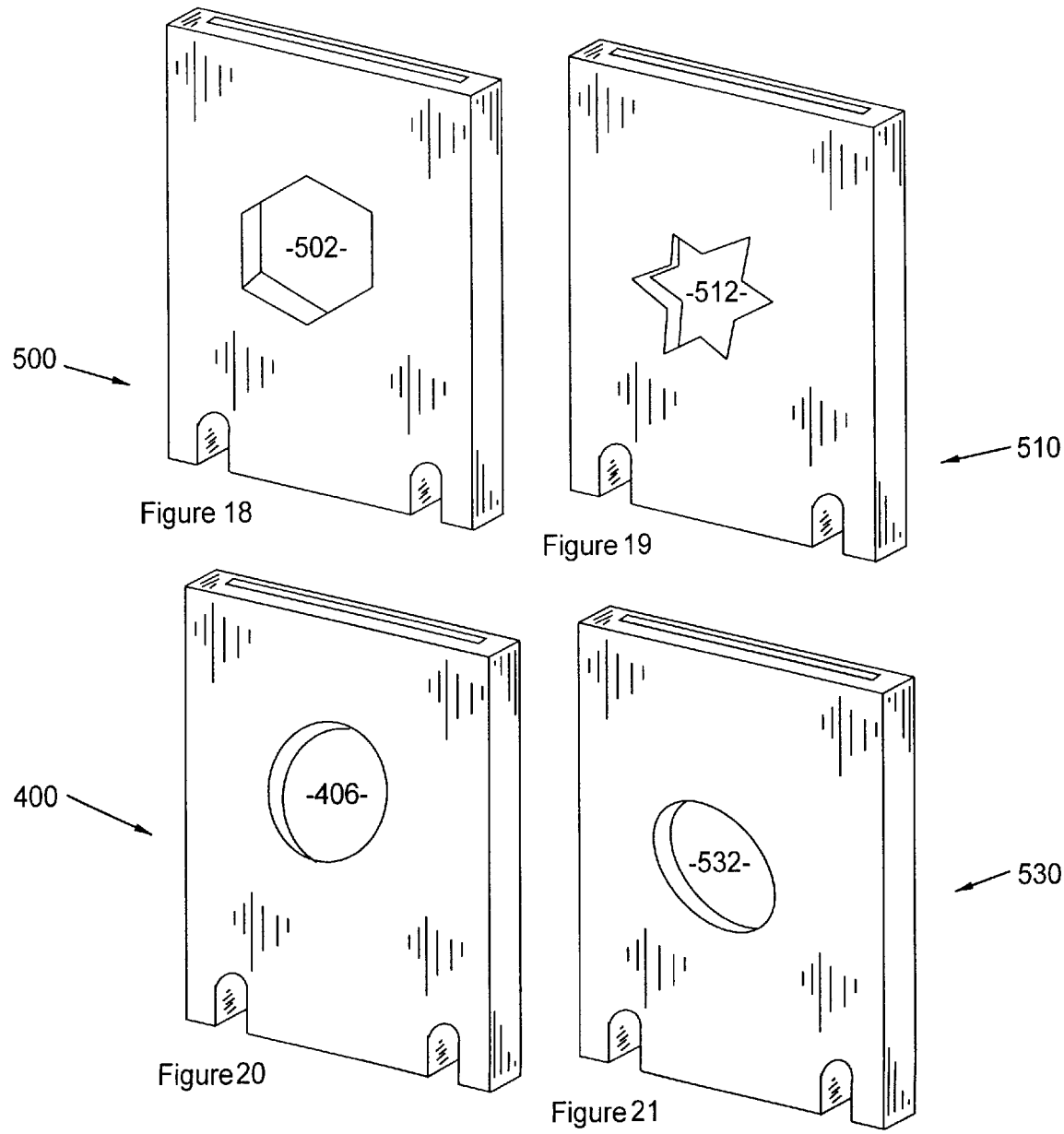

METHOD AND APPARATUS FOR ACCURATE COLOR READING OF MATERIAL HAVING VARIABLE DEPTH AND MOTIF

CROSS-REFERENCE TO RELATED PATENT APPLICATION

This application is a continuation-in-part of U.S. provisional patent application Ser. No. 60/097,411 filed Aug. 21, 1998, which is a continuation-in-part of 60/065,160 filed Nov. 12, 1997, both of which are incorporated herein by reference as though recited in full.

BACKGROUND OF THE INVENTION

1. Field of the Invention

The invention relates to a color measurement system and a device for use with the system, more particularly to the device and process of assigning a numerical value to the color of a material, to provide the ability to reproducibly test fabrics to determine the numerical color value.

2. Brief Description of the Prior Art

When manufacturers produce fabric, the ability to reproduce that color as close as possible in subsequent production runs is desirable. To this end, the spectrophotometer has been invented and is used throughout the fabric industry. The spectrophotometer assigns a numeric value to an individual fabric specimen, this value being achieved by light absorption of the specimen. This amount of light absorbed by an individual specimen is highly influenced by the pattern within the fabric. Therefore, in some fabrics, especially laces and prints, the readings can vary greatly depending upon the portion and/or direction of the fabric being viewed. Thus, a customer wishing to match a fabric purchased six months prior would read the numeric value of a piece of the fabric and send that number value to the manufacturer. Alternatively they could send the fabric sample to the manufacturer. Although manufacturers generally maintain records of dye lots, if the fabric sample was not mounted exactly the same as the original fabric at the initial reading, the subsequent readings can be inaccurate The disclosed system overcomes the difficulties of matching dye lots through the use of a closed system to manage fabric specimens and spectrophotometer readings. The disclosed system enables the manufacturer to reproduce the fabric color within variations acceptable to the customer. The system also produces an easy-to-use reference for the customers to reorder the same fabric as well as order a number of different fabrics dyed to match.

SUMMARY OF THE INVENTION

A card, generally rectangular, for maintaining a material in a fixed position is disclosed. The card has a body containing a fold line between its two ends which is cut into a V-shape or otherwise scored, to enable the card to fold in on itself. A pair of polygon windows within the body are placed on either side of the fold line. Sealing means, which can run vertically or horizontally to the card ends, or cover the entire card, are placed on a first side of the card secure the card to itself when folded. The material retained can be a fabric swatch overlaying one of the windows and secured within the folded card. In one embodiment the center point of the windows is equidistant from the fold line. The fold line can be approximately equidistant between the ends, forming two sections substantially equal size. Alternatively, the fold line can form asymmetrical sections that, when folded, still align the windows. A fabric recess preferable encompasses one of the windows. A fabric adhesive, preferably releasable, maintains the fabric swatch in position. The fabric adhesive can be placed within the fabric recess or encompassing an opposing window. At least a of portion of a second side of the card should be a light absorbing color. In one embodiment the card can contain receiving notches that are dimensioned to slideably maintain the card on a holder having flanges.

The cards are stored within a pocketed holder having pockets dimensioned to individually store multiple cards on a sheet. The holder is manufactured from a material that will shield the cards from UV light.

A holding plate is dimensioned to be received and affixed to a spectrophotometer and the cards. The holding plate has a length and a width. A slot, open at one end of the holding plate has a width greater than the window and length proximate the length of the holding plate. A window extends through the width window and is positioned to align with said spectrophotometer's window. A light interactive material, such as industry approved color tiles, as well known in the art, is placed adjacent the window opposite the spectrophotometer. The interactive material is placed in a interactive material receiving area that is dimensioned to receive the material. In the preferred embodiment the receiving area is recessed and extends from the front surface for a predetermined distance into the width to form a back wall. A lip spaced from the back wall, extends around at least a portion of the recessed area perimeter. A portion of the slot is open to the recessed area. The holding plate can be manufacture from one piece of the front surface and said back wall can be separate portions and affixed together to form the body.

To use the card and holding plate combination a specific, repeated pattern within said fabric is chosen, centered over a die cutter and cut to create a first specimen. This is repeated to create at least one customer specimen. The fabric adhesive covers are removed from the submit holding card, the first specimen centered over holding card window and placed onto the fabric area adhesive. The permanent adhesive covers are removed and the holding card folded at the fold line and the permanent adhesives to themselves to maintain the holding card in a closed position. The holding card is placed into holding plate and a color reading of the specimen taken. The color reading is stored within the spectrophotometer and printed for affixing to readings the holding card. This is repeated for each specimen. One specimen is retain as a control specimen for reference and at least one other specimen is forwarded to the customer for future ordering. The color reading affixed to the card reflects a numeric value assigned to the fabric swatch by the spectrophotometer and enables subsequent fabric runs to be compared and matched to the control specimen. The customer's specimen enables the customer to compare new and current fabric colors to the customer specimen for reorder and verification of ordered color.

A die cutter for aligning and cutting specimens has a body with a base and a support arm. A cutting blade is affixed to a moveable arm which moves along the support arm through the use of drive means. Preferably a lit cutting pad is adjacent the base and positioned to receive the cutting blade when brought, by the moveable arm, in contact with the cutting pad. Contact of the blade to the pad cuts the specimen placed on the cutting pad after which the arm moves away from the cutting pad to permit removal of the specimen. Preferably the lit pad is a hollow base containing a light source and having a transparent top panel with marking indices. The cutting base, a resilient material to receive said cutting blade, encompasses the transparent top panel. The light source reflects through the transparent top panel, enabling a specimen to be aligned along the indices prior to the cutting blade contacting the cutting base to cut the specimen. Alternatively, the light source is proximate the cutting blade. Preferably the cutting base is removable to permit replacement.

The above card and holding plate provide a fabric color reading and management system to permit reproducible readings of fabric specimens. The spectrophotometer readings are affixed to one side of the card to provide data of the color readings at time of mounting. The opposite side of the card is provided with the company name, specimen and batch identification numbers, etc. The submit holding card is placed into the submit holding plate for reading with the spectrophotometer. The submit holding plate does not require removal after each use, therefore permitting rapid, easy changing of the holding cards. A holding sheet is used to receive the submit holding cards in a UV protected environment.

DESCRIPTION OF THE DRAWINGS

The advantages of the instant disclosure will become more apparent when read with the specification and the drawings, wherein:

FIG. 1 is a plan view of an open submit holding card in accordance with the present invention;

FIG. 2 is a side view of the open submit holding card of FIG. 1;

FIG. 3 is a side view of the open submit holding card of FIG. 2 with the fabric in place;

FIG. 4 is a side view of the submit holding card of FIG. 3 in the folded position;

FIG. 5 is a side view of the submit holding card of FIG. 4 with the frame sealed together for use and subsequent storage;

FIG. 18 is a perspective view of the back of the submit holding plate of FIG. 13 having a hexagonal cutout;

FIG. 19 is a perspective view of the back of the submit holding plate of FIG. 13 having a star shaped cutout;

FIG. 20 is a perspective view of the back of the submit holding plate of FIG. 13 having a circular cutout;

FIG. 21 is a perspective view of the back of the submit holding plate of FIG. 13 having a elliptical cutout;

DETAILED DESCRIPTION OF THE INVENTION

Figure 6:
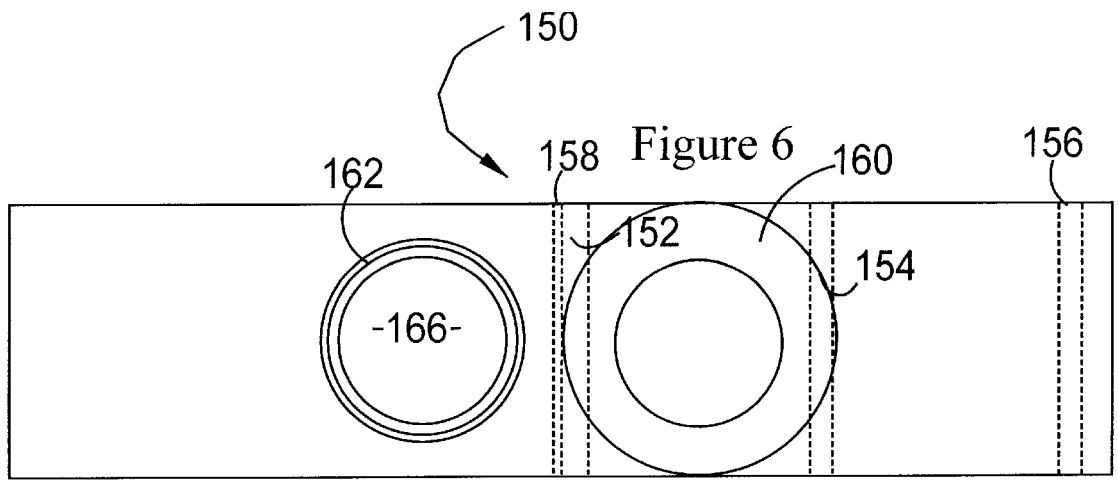
FIG. 6 is a plan view of an alternate embodiment of a submit holding card.
Figure 7:
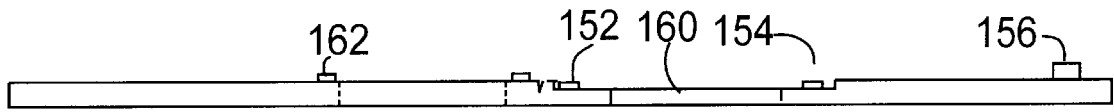
FIG. 7 is a side view of the submit holding card of FIG. 6.
Figure 8:
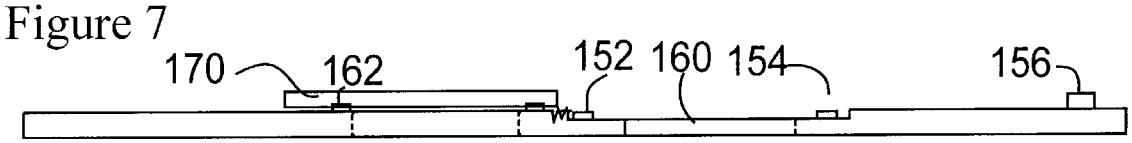
FIG. 8 is a side view of the submit holding card of FIG. 7 with a fabric sample in place.

Spectrophotometers are used by fabric companies to "read" color and convert the color to numeric values, thereby assigning an absolute value to a specific color. The spectrophotometer software is able to compare specimens and, through visual and numeric readouts, inform the user of the color variations between two specimens.

These numeric readings indicate to what degree, and basic color range, a sample specimen varies from a control specimen and whether it falls within preprogrammed tolerances. These readings have provided substantial benefits to the fabric industry in standardizing acceptable tolerances and removing the personal subjectivity to color comparisons. To provide controlled calibration between different machines, heat-treated, industry controlled, tiles are used to ensure that each machine reads colors in either the same or, at the least, an identifiable manner. The treated tiles do not fade over time and therefore are ideal for long term use. Additionally, as the treated tiles are used for calibration, their use maintains a system consistency that may be compromised using other backings. Although black has proven to provide the most consistent readings with all fabric colors, due to its light absorption capabilities, it should be noted other colors can be used.

Problems have arisen, however, in color reading fabrics that do not have a consistent knit or contain fibers having varied finishes, deniers, luster, thickness, patterns, etc. A popular example of this material would be lace, or other fabrics, in which multiple fibers are, in some cases, used to provide the three dimensional, open patterns. A spectrophotometer reads multiple points within an area, averages each reading within the area, and produces a final reading based upon, or variable relative to, the number of layers, pattern density and yard components. Additionally, for stretchable materials, whether lace or fabric, the degree to which the material is stretched affects the color reading. This has presented problems in assuming the repeatability and consistency of color measurement and matching subsequent dye lots to the control color. A mismatched dye lot creates lost profits for the industry due to project rejections for shade deviation, and/or returns for re-dyeing of the fabric. The disclosed method and apparatus enables materials that do not have a consistent density to be accurately read and compared to a control specimen.

The following embodiments illustrate the sample specimens in various configurations. Some of the embodiments allow the material to be rotated while others require that the material be placed in the exact rotational plane as the control specimen. Whether there is a need to exactly match the material along the rotational plan is dependent upon the pattern of the material being read.

In order to enable repeated, reproducible testing and comparison of fabric samples, it is critical that each sample read is the same thickness, pattern direction and pattern location. This is most critical when testing fabrics, such as lace, where the three dimensional pattern, as well as direction, varies so dramatically from section to section. Although lace is one of the more dramatic examples of the criticality associated with exact, reproducible placement, other fabrics also require careful placement. The submit holding card 100, illustrated in FIGS. 1–5, provides a card that permits, in conjunction with the submit holding plate disclosed hereinafter, material to be viewed in a spectrophotometer in a reproducible manner. The submit holding card 100 illustrated in these figures is a rectangular configuration containing a pair of windows 116 and 112. The windows 116 and 112 must be positioned within the submit holding card 100 to ensure alignment with the viewing area of the submit holding plate as disclosed herein. A fold line 114, in the illustrated embodiment, divides the card 100 at the center point to allow for easy folding. Alternatively, the fold line can be placed to form an asymmetrical card, however the windows must align to permit the light to pass through from the spectrophotometer to the tiles. The windows 116 and 112 are positioned so that when the holding card 100 is folded at the fold line 114, the windows 116 and 112 are aligned with one another, having nearly identical center points from the fold line 114. Although the windows 112 and 116 have approximately the same circumference, however in some applications one window could have a greater circumference, or a different center point, as long as the light reflecting through the windows enable accurate readings of the specimen. The card 100 has adhesion strips 108 and 120 that run along the length of the card 100 from end 102 to end 104. The adhesion strips 108 and 120 are generally a double-sided tape with a removable, protective layer, however other pressure sensitive adhesives, as currently known in the art, can be used. Surrounding the window 116 is the recessed fabric retaining area 118 to recess the fabric 140 slightly to permit even contact between the adhesion lines 108 and 120. In this embodiment, a pressure adhesive 110 surrounds the window 116, securing the fabric swatch to the card 100. The adhesive 110 can be any pressure adhesive used for the adhesion lines 108 and 120 or a releasable adhesive as used for Post-It Notes®. The fabric retaining area 118 also helps to maintain the fabric swatch in the intended position, preventing shifting and sliding. Alternatively, the adhesive can be placed around the window 112, opposite the recessed retaining area 118. The fabric would then be placed over the adhesive and the recessed portion placed over the fabric. Although adhesives are referred to herein, other means of sealing the fabric to the card and the card back to face, can be used. These can include edging the card in tape, staples, or other means applicable to sealing the front and back to the card 100 together without preventing its intended use.

The notational exterior 122 can be, if desired, a light color to enable notes to be clearly visible. In the event the area is intended for imprinting purposes, the notional exterior 122 can be any color desired. At least a portion of the holding card exterior 124 must be a calibrated color, generally black, to allow for machine calibration. Although it is not necessary for the entire surface of the exterior 124 to be the calibrated color, it is recommended that at least one quarter inch surrounding the window 112 be the calibrated color. It is critical that any surface that is seen by the spectrophotometer be the calibrated color to avoid any light reflection once the card 100 is placed in the spectrophotometer. Therefore by providing at least a portion of the exterior 124 in the calibration color, dimensioning errors affecting readings can be compensated for. Black is the preferred color as it provides the least distortion of feedback to the spectrophotometer, however other non-reflective colors can be used.

As can be seen in FIG. 3, the fabric 140 is placed to overlap the window 116, adhering to the surrounding adhesive 110 of the fabric retaining area 118. The placement of the fabric 140 is critical, as turning or placing the fabric 140 off center in subsequent frames 100 will affect the readings. The fabric 140 is illustrated in FIG. 3 placed directly onto the adhesive 110, however in some instances it is preferable to position the fabric 140 over the window 112 prior to sealing.

Once the fabric 140 is secured to the retaining area 118, the frame 100 is folded, as illustrated in FIGS. 4 and 5. The alignment between the windows 112 and 116 can clearly be seen in this figure. To allow for increased ease of alignment, the fold 114 is placed mid way between the end 102 and the end 104. Thus, when the user is folding the frame 100, the ends 102 and 104 will be aligned to prevent any re-creasing or shifting. In FIG. 5 the adhesive 120 has been sealed to itself and the fabric 140 firmly sealed within the frame 100. The sealing is accomplished by simply pressing together the adhesive 120. By encompassing the fabric within the frame 100, the fabric 140 is locked in position and will not be inadvertently repositioned during normal usage in conjunction with the color spectrophotometer.

An alternate embodiment is illustrated in FIGS. 6–9 where three adhesive strips 152, 154 and 156 are used to secure the frame 150. The adhesive strips 152, 154 and 156 in these figures run the width of the frame 150 rather than the length, as illustrated in FIGS. 1–5. Two of the adhesive strips 152 and 154 overlap the recess 160, thereby serving to retain the fabric 170 in the desired position within the card 150. In this embodiment the releasable fabric adhesive 162 has been placed on the panel side 164 to initially maintain the fabric 170 in position. The releasable adhesive 162, such as used for Post-it® notes, permits the fabric 170 to be repeatedly removed and replaced to ensure optimal placement. Although the fabric 170 can be held in place during closure and sealing of the card 150, it is more awkward and permits the possibility of the fabric slipping during sealing. Attaching the fabric 170 directly to the adhesives 152 and 154 weakens the permanent adhesive in the event the fabric 170 needs removal and replacement. It should be noted that although the releasable adhesive 162 is illustrated in a complete circle, the adhesive can be applied to several places around the periphery of the window 166. Additionally, the releasable adhesive can be incorporated in any of the embodiments disclosed herein. The permanent adhesive used herein can be a hot melt glue for rapid, strong bonding or, for convenience and ease of use, a pressure sensitive adhesive strips as described heretofore. The fabric 170 is secured to the submit holding card 150, as disclosed heretofore; the card 150 folded at fold line 158 and sealed, thereby locking the fabric 170 in place.

Figure 11:
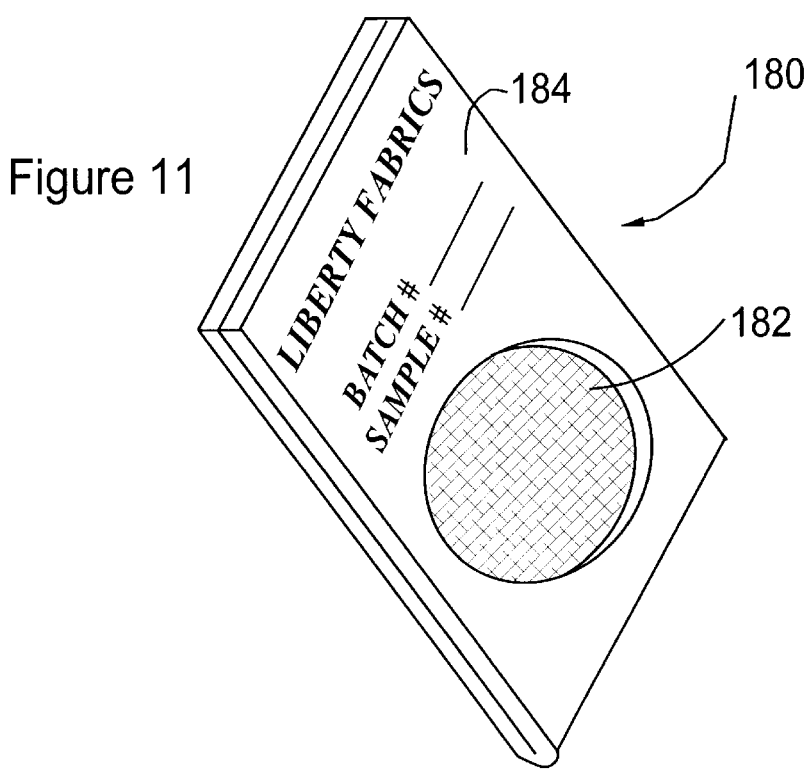
FIG. 11 is a perspective view of the submit holding card of FIG. 8, folded and sealed for use and subsequent storage.
Figure 9:
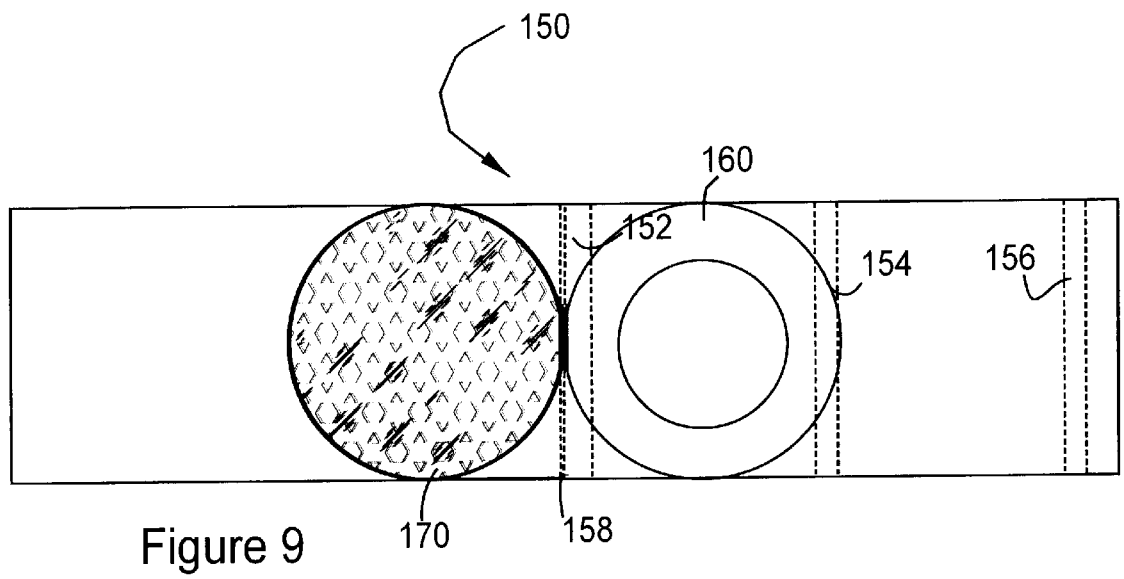
FIG. 9 is a plan view of the submit holding card of FIG. 8 with a fabric sample in place.
Figure 10:
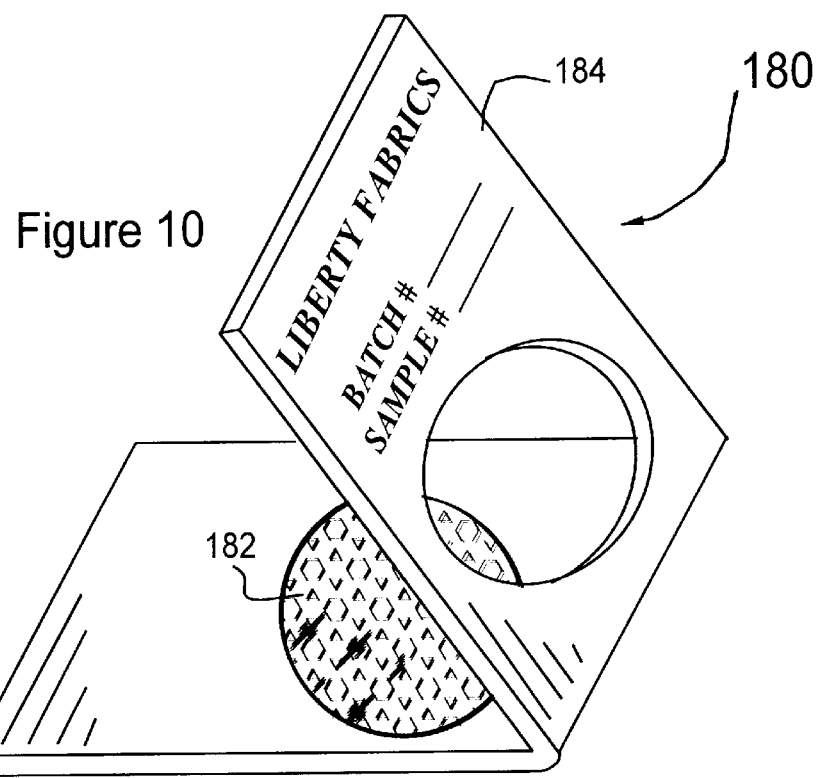
FIG. 10 is a perspective view of the submit holding card of FIG. 9 being folded along a fold line.
Figure 12:
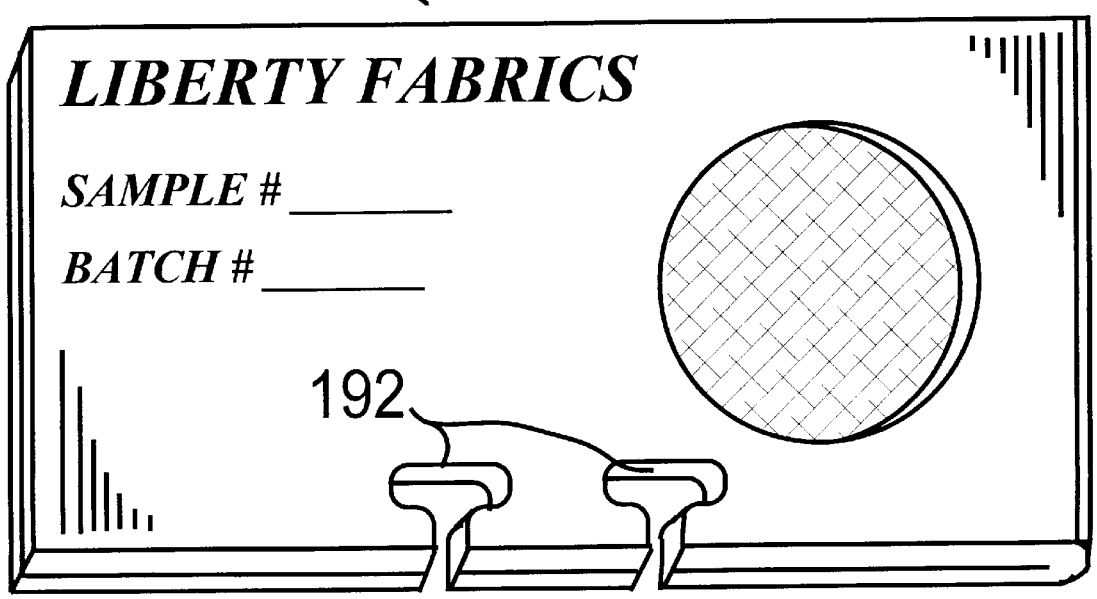
FIG. 12 is a perspective view of a further embodiment of a submit holding card of the present invention folded and sealed for use and subsequent storage.
Figure 16:
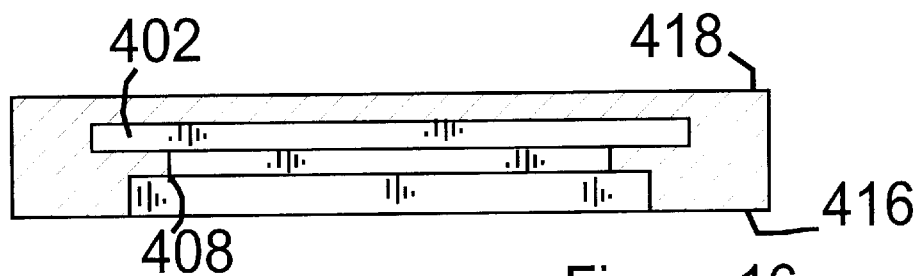
FIG. 16 is cut away top view of the submit holding plate of FIG. 13.

FIGS. 10 and 11 illustrate folding of the card 180 as well as the appearance of the folded, sealed card 180. The face 184 of the card 180, as well as other embodiments herein, can be either preprinted with specific company data or left blank for notes. Optimally, the face 184 of the card 180, as well as all other frames disclosed herein, are printed with the company name, batch number and sample number. The placement of the batch and sample number on the face of the card provides for ease and efficiency in locating the specific specimen at a later date. The single layer of fabric 182 is locked within the card 180 to allow for storage until required for later use. These figures are representative of one exterior achievable from the foregoing embodiments in their folded and sealed configuration. In FIG. 12 an alternate appearance is illustrated wherein the card 190 is provided with receiving slots 192 which are configured to be received in a holder similar to that used with address cards. Other configurations meeting the criteria set forth herein will become apparent to those skilled in the art.

Figure 22:
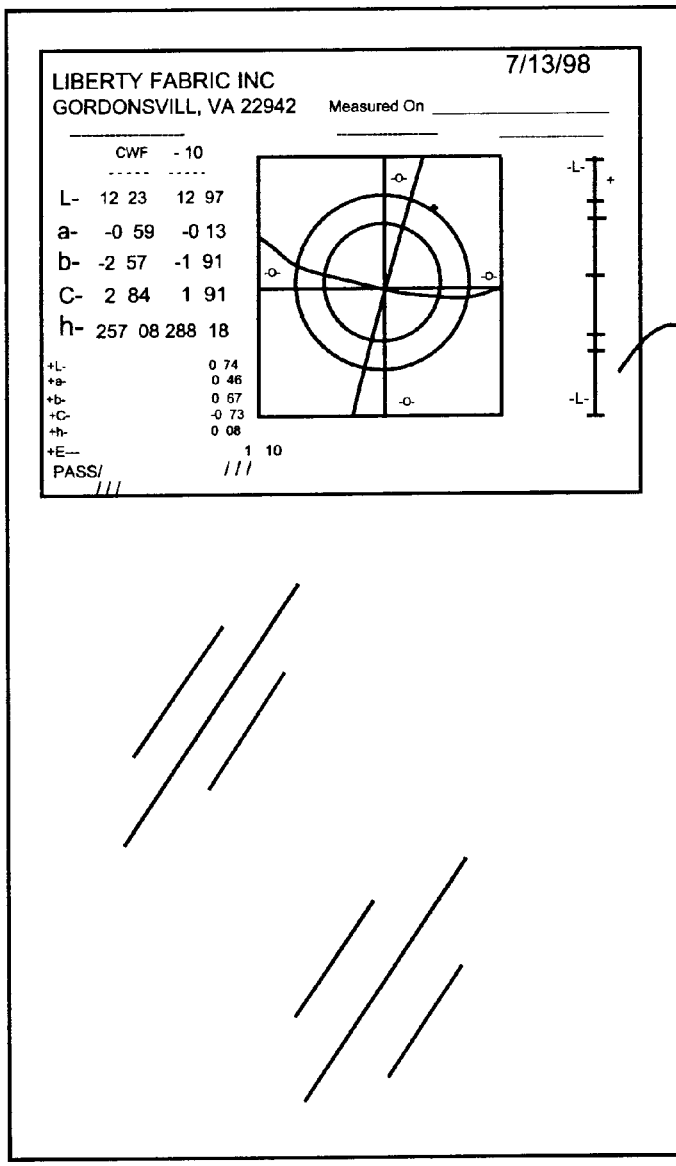
FIG. 22 is a front view of an identification label and color data graph used in conjunction with the disclosed system.

In order to further facilitate the coordination of the sample colors between the manufacturer and the customer, the disclosed system includes a spectrophotometer printout of the specimen contained within the submit holding card. An example of this printout is illustrated in FIG. 22 wherein, in this embodiment, a label 142 is printed containing sufficient information to reproducibly identify the contained specimen. The label 142 can be placed on either side of the card 100, however, care must be taken to avoid obstructing the windows.

Figure 13:
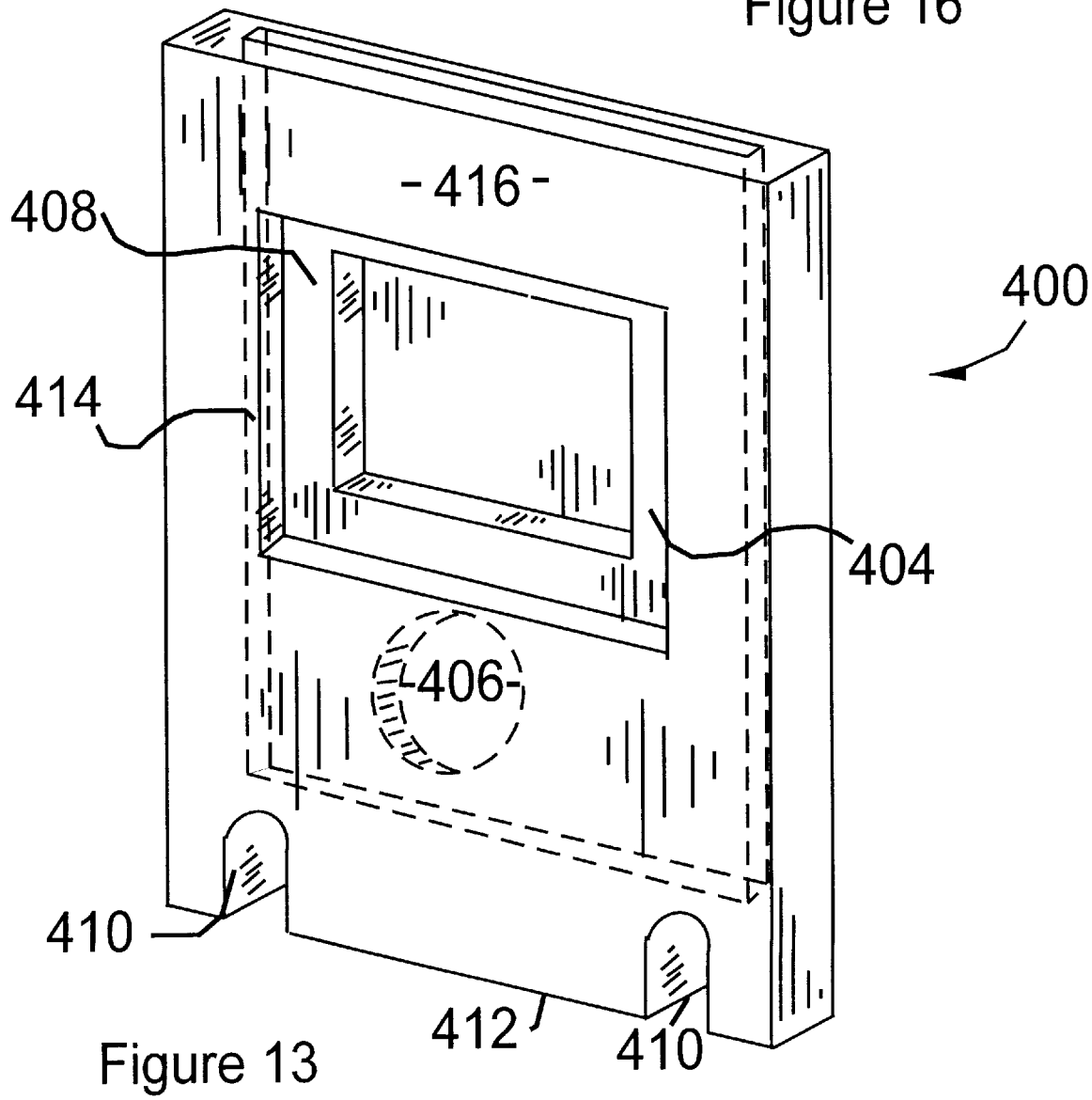
FIG. 13 is a perspective view of the front of the submit holding plate of the instant invention for use with a spectrophotometer.
Figure 15:
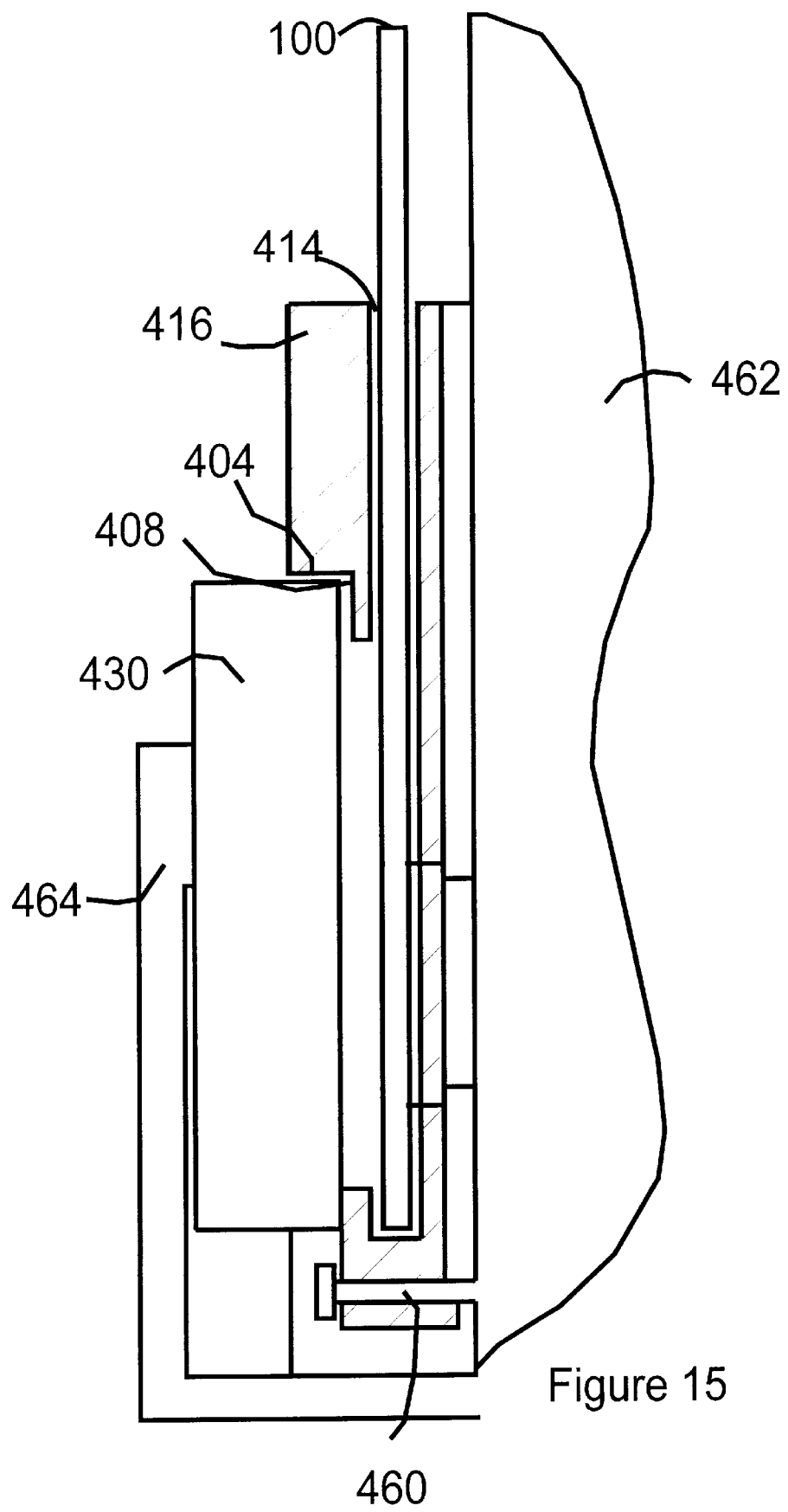
FIG. 15 is a cutaway side view of the submit holding plate placed within a spectrophotometer.
Figure 17:
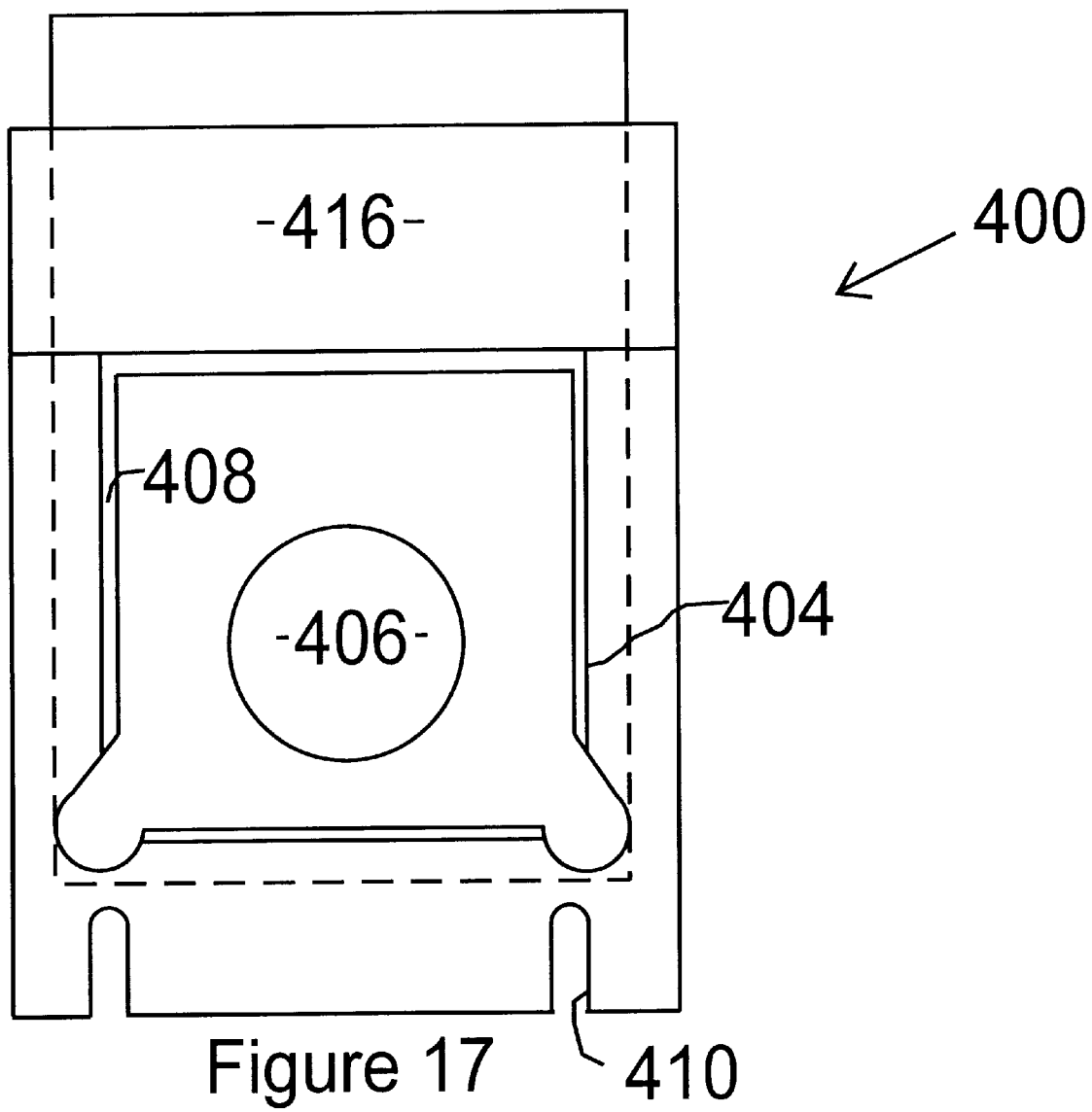
FIG. 17 is a front view of the submit holding plate of FIG. 13.

FIGS. 13 and 17 illustrate the disclosed submit holding plate 400 into which the submit holding card 100 is inserted. The base 412 of the submit holding plate 400 is designed with receiving arches 410 that are configured to interact with the port of the corresponding spectrophotometer. It should be noted that the placement and configuration of the receiving arches 410 will vary to maintain compatibility with specific machines. A receiving notch 402 provides access to the submit holding card receiving slot 414, at approximately the center of the submit holding plate 400. The dimensions of the receiving slot 414 are dimensioned to receive any of the submit holding cards described heretofore. The face 416 of the template 400 is provided with a window 406 in the back wall 418 that is aligned with the windows 112 and 116 of the holding card 100, thereby enabling light from the spectrophotometer to read the fabric. The window 406 of the submit holding plate 400 is surrounded by recess 404, which is rimmed on at least three sides by lip 408. The periphery of the recess 404 is dimensioned to receive the commercial calibrating tiles 430, as illustrated in FIG. 15. The lip 408 prevents the calibrating tiles 430 from coming in contact with card 100, thereby permitting the card 100 to be slipped in and out without causing damage to the card or fabric.

In FIGS. 18–21 various designs of light ports are disclosed. In FIGS. 18, 19 and 21, the template 500 uses a hexagon light port 502; template 510 a star shaped light port 512 and template 530 an elliptical light port 532, respectively. The circular light port 408 within the template 400 is illustrated in FIG. 19. For use herein circular is define as a polygon having infinite sides. The use of non-circular shapes within the templates provides an advantage in the positioning of the fabric. By using a non-rotatable pattern, or pattern easily identifiable, the direction of the threads and pattern is more easily maintained consistent.

Figure 23:
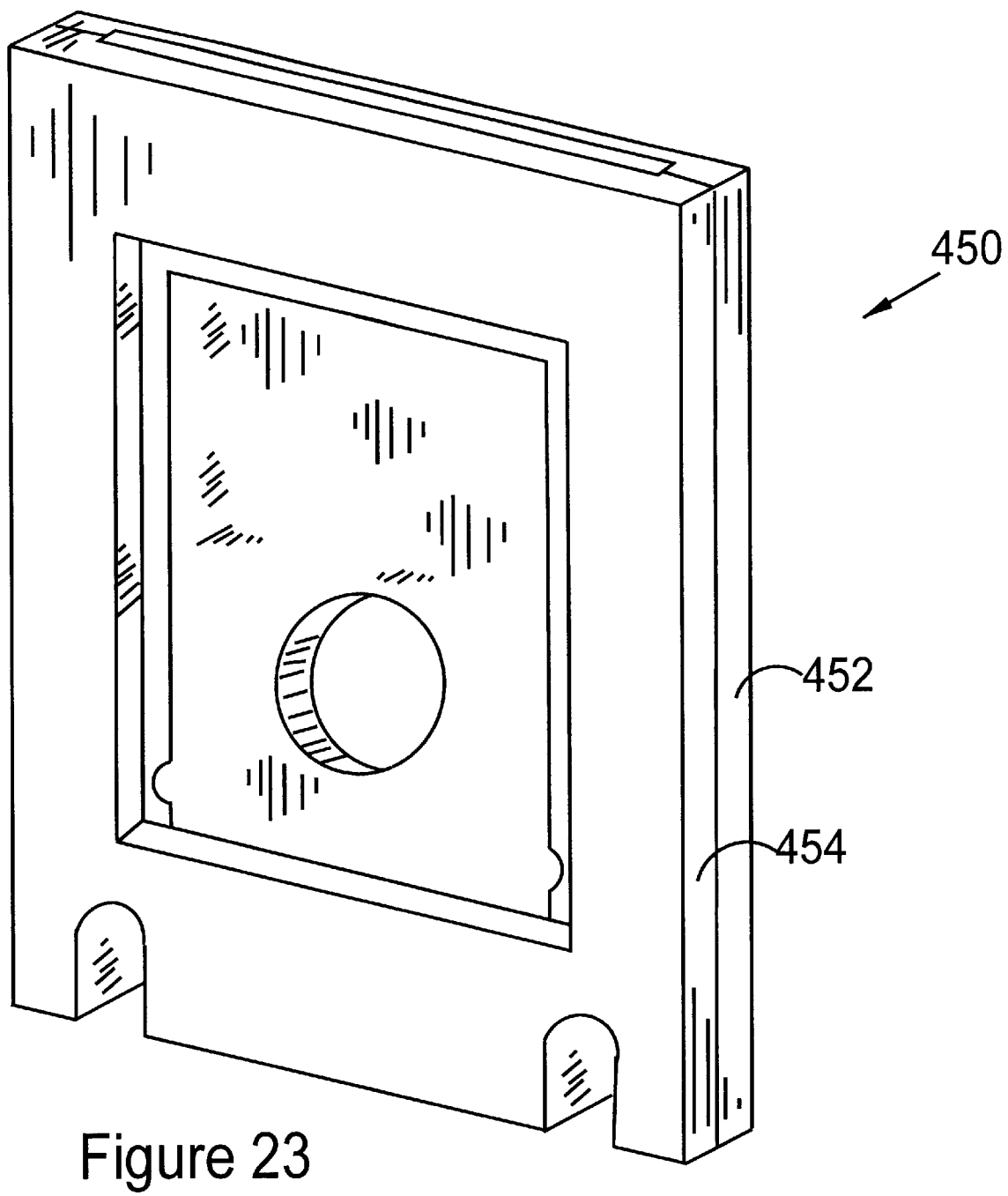
FIG. 23 is a perspective view of an alternate holding plate manufactured from two parts and affixed together.

The template 400 illustrated in FIG. 13 is a single piece, molded unit. The template 450 of FIG. 23 is manufactured from a face plate 454 and back plate 452, which are then secured together by means applicable to the material of manufacture The construction and dimensioning of the template 450 remains the same as that of the template 400 with respect to positioning of the receiving notch, receiving slot, recess, lip and light window.

Figure 14:
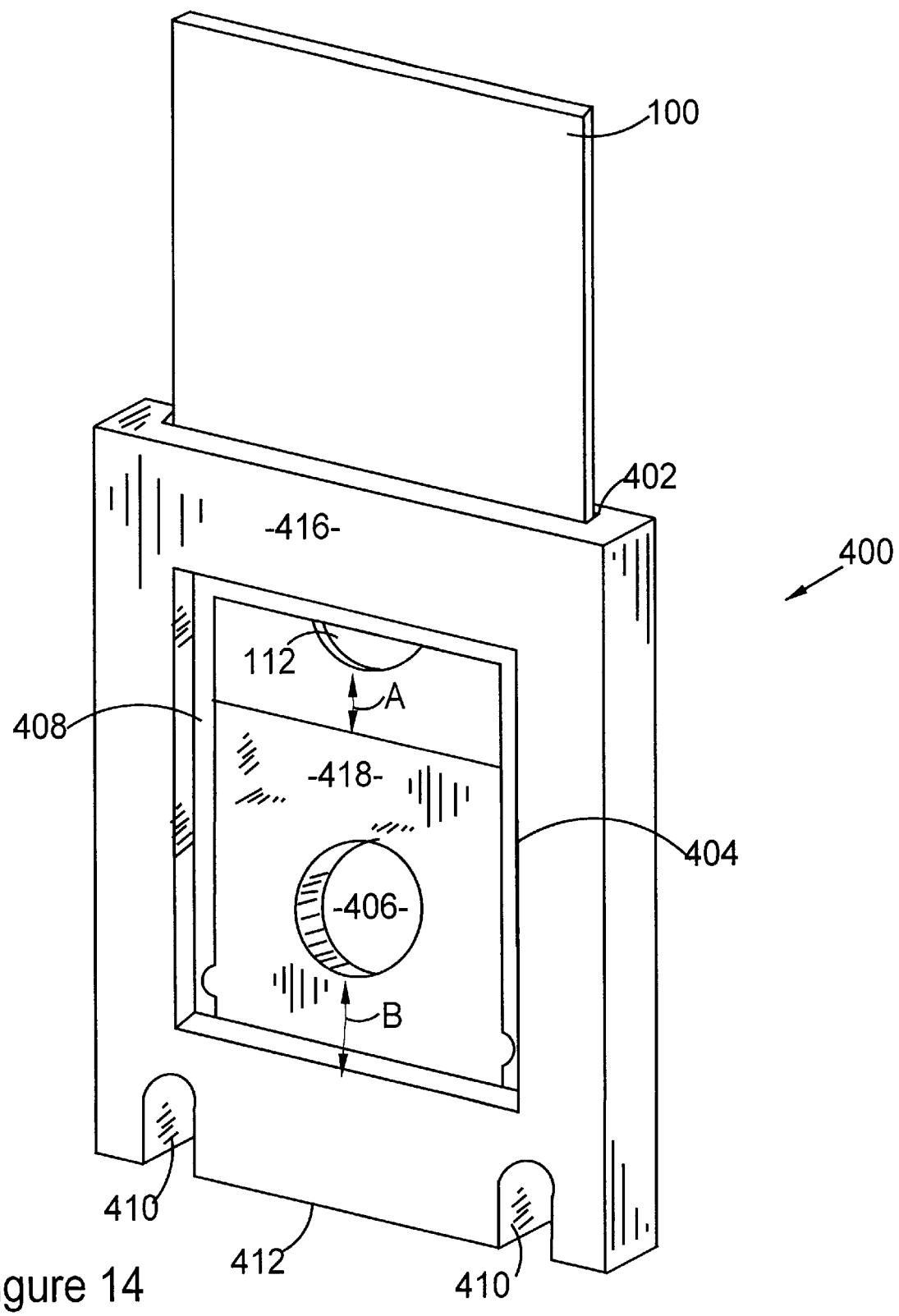
FIG. 14 is a cutaway perspective view of the front of the submit holding plate of FIG. 13 with the fabric frame partially inserted.

In FIG. 14, the submit holding card 100 has been partially inserted into the holding plate 400 to illustrate further the relationship between the holding plate 400 and the card 100. Once the submit holding card 100 is in position, the fabric window 112 will be aligned with the light port 406. The dimensioning between the holding card 100 and the holding plate 400 is critical to ensure that the window 112 of the card 100 is in alignment with the plate window 406. To accomplish this dimensioning, the distance "A" between the bottom of the window 112 and the end of the card must be equal to that of the distance "B" between the bottom of the plate window 406 and the base of the slot 414. To minimize movement of the card 100 within the holding plate 400, slot 414 must have a periphery only slightly greater than that of the card 100. This prevents the window 112 from coming out of alignment with the window 406. By placing the window 406 off-center, the spectrophotometer will not be able to read the fabric if the card 100 is placed upside down, eliminating user error. In order to prevent the card 100 from being reversed, the black surface of the spectrophotometer exterior 124 of the card 100 provides an indication of insertion direction. To further prevent user error, instructions can be placed on the indication exterior 122 of the card 100.

FIG. 15 illustrates a side view of the submit holding plate 400 and submit holding card 100 inserted into the spectrophotometer 462. The recesses 410 are placed on the spectrophotometer holding screws 460 and maintain a flush connection with the spectrophotometer 462 through a bracket 464. The calibration tiles 430 are placed within the recess 404, abutting the lip 408. The bracket 464 is part of the spectrophotometer 462 and is dimensioned to maintain the calibration tiles 430 and prior art specimen holder in place for measuring the color values of the fabric.

The disclosed system permits the submit holding plate 400 to remain in position within the spectrophotometer 462 without the constant removal required by prior art devices. The cards 100 are simply slipped in, read, and removed, with the consistent placement of the specimen being maintained. The inclusion of the numeric values for the specimens also serves to indicate when the specimens have discolored or been soiled. If the color reading does not fall within known tolerances, it is an indication that the specimen no longer retains the original color. At that point a new specimen should be matched and mounted.

Figure 26:
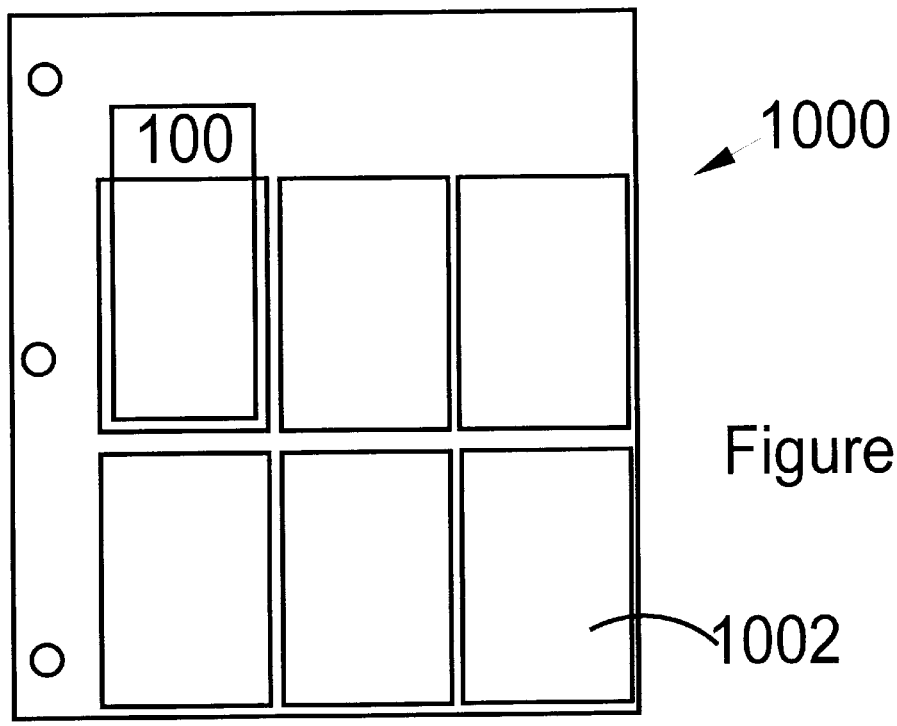
FIG. 26 is a front view of the protective holding pages for the disclosed submit holding cards.

In order to minimize color distortion the, specimen containing, submit holding cards must be placed in a material that is chemically inert to the fabric. Material treated with some UV stabilizers will react with the swatch effecting the color. An example of an acceptable material is BHT, and other materials meeting the criteria set forth herein will be known to those skilled in the art. An example of a notebook holder 1000 is illustrated in FIG. 26 wherein the fabric frames 100 are inserted into the pockets 1002. This configuration is for example and a greater or lesser number of pockets 1002 can be utilized. The pockets 1002 must be slight larger than the fabric frames 100 to allow the frames 100 to be easily inserted and removed without bending or distortion. It is preferable that the notation portion of the frame 100 is not covered by the frame 100 below to allow for viewing of the pertinent information while all frames 100 are in the holder 1000.

As repeatedly noted above, matching patterns of the cut specimens is critical. In standard dye cutters the cutting base and the cutting dye are only a couple of inches apart. This makes it difficult to repeatedly center the original cut and align subsequent cuts with the original. In addition to the visibility problem, it is also difficult to align a pattern, as there are no markers provided on the cutters.

Figures 24, 25:
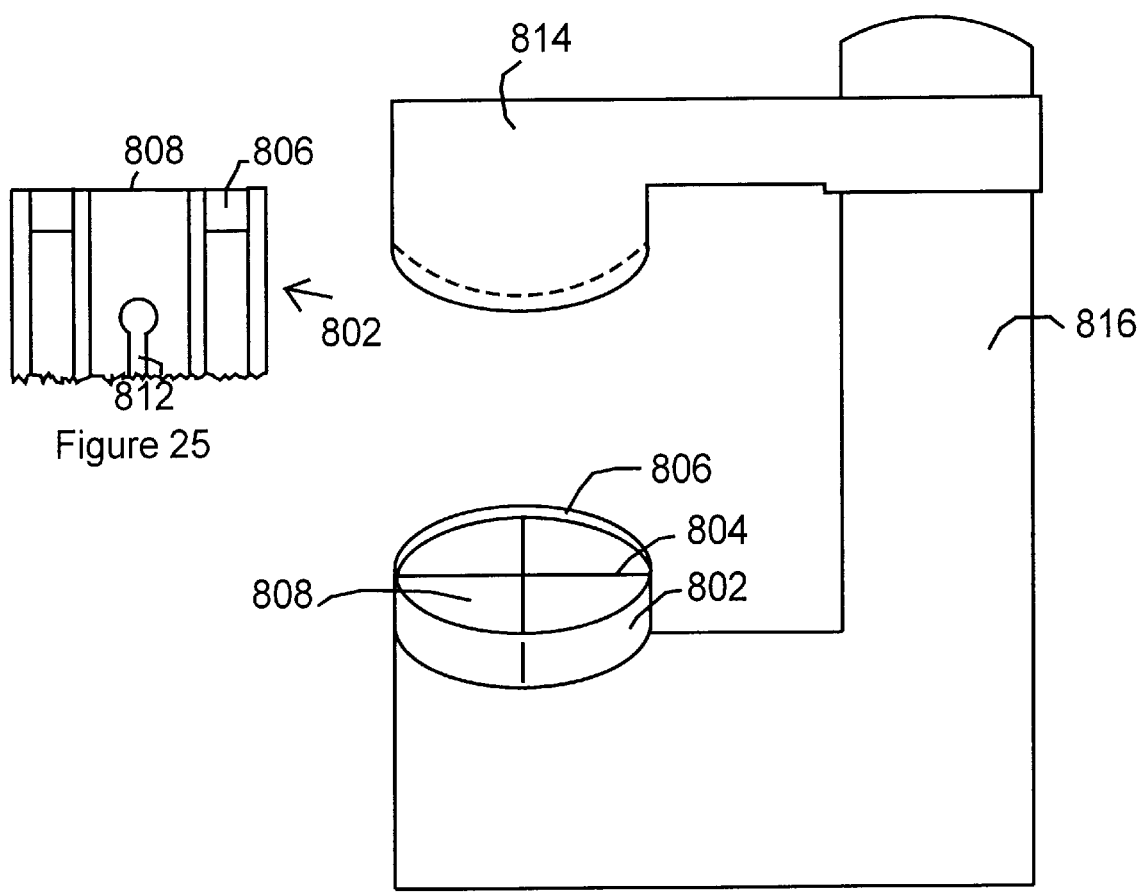
FIG. 24 is a side view of the lit base dye cutter.
FIG. 25 is a cutaway side view of the base of the dye cutter of FIG. 24.

To overcome this problem, the preferred die cutter 800 illustrated in FIGS. 24 and 25, provides visibility, as well as marking indicators for fabric alignment. The die cutter 800 is provided with a lit base 802 that contains a clear, or opaque center light panel 808. The light panel 808 is provided with cross hairs 804, although other types of indices can be used. The light panel 808 is surrounded by a cutting base 806 dimensioned to come in contact with the cutter blade 810. The cutting base 806 is manufactured from a resilient material, such as rubber or plastics, which can structurally withstand repeated contact with the cutting blade 810. In the preferred embodiment the cutting base 806 is removable, allowing for easy replacement. The lit base 802 is provided with a bulb 812 to highlight the cross hairs 804 and make fabric alignment and realignment easier. The cutter head 814 moves up and down along the arm 816 of the cutter 800, and can be powered by electricity, batteries, manual levers or other means known in the art. The arm 816 preferable has a length sufficient to enable the cutter head 814 to away from the cutter pad a sufficient distance to permit easy specimen alignment. Most die cutters provide little space to position the specimens and are designed for a simple cutting procedure, not specimen alignment. It is preferable that a non-manual method, such as hydraulics, be used to permit the user to maintain the fabric in the desired position. The hydraulics can be operated by a switch proximate the user's hand, a foot peddle, or other methods known in the art. The exact body design of the cutter 800 is not crucial and the novelty lies in the ability to align a fabric sample in a predetermined location and repeatedly place the fabric in the same location.

Figure 27:
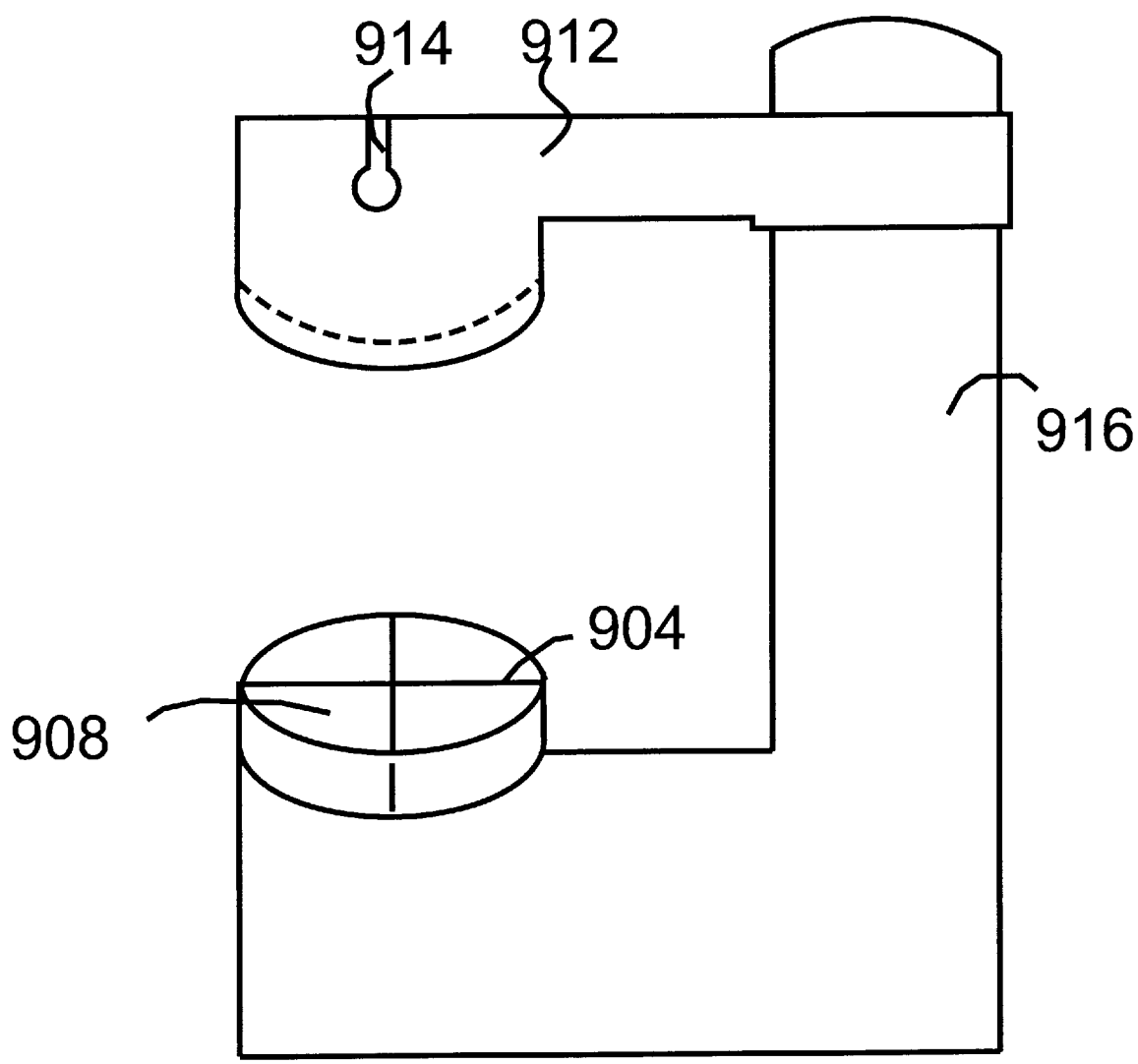
FIG. 27 is a side view of a top lit dye cutter.

In an alternative embodiment as illustrated in FIG. 27, the light 914 can be contained in the center of the cutting pad 912 and reflect downward onto the cutting pad 908. Cross hairs 904 are used as the locator and, since the light source is from above, the color contrast between the cross hairs 904 and the cutting pad 912 should be a distinct as possible. Preferably the cutting pad 912 is replaceable to account for normal wear. The cutting pad 912 moves along the support 816 as described heretofore.

It is important in reading many fabrics that the exact direction, i.e. back to face and up and down, be the same between the control specimen and the customer specimen. In order to accurately read the color of lace and other such materials, the pattern within the sample specimens must coordinate exactly with the control pattern. In other words, if the center of a flower is used as the center point for the control specimen, then the sample specimens must be read with the center of the flower as the center point. Therefore alignment becomes critical and properly evaluating the color is determinant upon matching the specimen center points.

Lace poses a unique challenge to color reading which is not seen in other types of fabric. It is critical that only a single layer of lace be used as multiple layers alter the light readings from specimen to specimen. Further, when placing the material into the recessed area, the material must be placed in a relaxed position as any stretching will alter the material reading. Due to the infinite fiber variations available when manufacturing these materials, the exact style must be compared. This means that although the lace used for the body of a garment and the trim for the same garment are the same color and have almost the same fiber content, they will not read the same. A single change in denier, finish, texture, etc., will alter the light readings enough to provide a false reading. The spectrophotometer assigns a value to a control specimen and then reads and compares subsequent specimens to the control specimen. Therefore, it has been found in lace, and similar fabrics, that the subsequent specimens must have the same center point as the control specimen. In order to facilitate the cutting of the control and subsequent specimens, plates and guides have been developed for use with the disclosed templates. The disclosed fabric color standardization system uniquely provides for consistent and reliable color matching of fabrics from different sources and/or different fabric runs.

An example sequence that will produces accurate color readings follows the following flow chart:

CHOSE A SPECIFIC, REPEATED PATTERN WITHIN THE FABRIC

PLACE FABRIC OVER DIE CUTTER

CENTER PATTERN

DIE CUT FABRIC

CUT SHAPE CREATES A CONTROL SPECIMEN

PLACE FABRIC OVER DIE CUTTER

CENTER CHOSEN PATTERN TO REPRODUCE CONTROL SPECIMEN

DIE CUT FABRIC

CUT SHAPE CREATES A CUSTOMER SPECIMEN

REMOVE ADHESIVE COVERS FROM SUBMIT HOLDING CARD

CENTER CONTROL SPECIMEN ON HOLDING CARD WINDOW

PLACE CONTROL SPECIMEN ONTO RETAINING AREA ADHESIVE

REMOVE PERMANENT ADHESIVE COVERS

FOLD HOLDING CARD AT CREASE LINE

SEAL ADHESIVES ONTO THEMSELVES

MARK IDENTIFICATION NUMBERS ONTO CARD

PLACE HOLDING CARD INTO HOLDING PLATE

TAKE COLOR READING OF CONTROL SPECIMEN

STORE COLOR READING OF CONTROL SPECIMEN

PRINT COLOR READINGS AND AFFIX TO HOLDING CARD

RETAIN CONTROL SPECIMEN FOR REFERENCE

PLACE CUSTOMER SPECIMEN IN HOLDING CARD

PLACE CUSTOMER HOLDING CARD IN HOLDING PLATE

TAKE COLOR READING OF CUSTOMER SPECIMEN

In the preferred embodiment of the complete system, two fabric swatches are cut from the same control panel. Both of these swatches are mounted onto submit holding cards and marked appropriately. One of the cards, or the control card, is stored at the manufacturer's location and the other is given to the customer with the first run. In this way, the customer and manufacturer both have a swatch from the identical run against which to compare subsequent runs.

As the swatches are read through use of a spectrophotometer, subjectiveness on the part of the viewer is eliminated. The colors either fall into a predetermined numerical tolerance or they don't. As the manufacturer has the control specimen from the identical dye run, each subsequent run can be tested and verified that it matches prior to shipment to the customer. This prevents customer returns and dissatisfaction by only shipping fabric falling within the numeric tolerances.

Although the foregoing description has been referring to reading and assigning a numeric value to a fabric specimen using a spectrophotometer, the disclosed system can be used with other types of light reading equipment. The holding plate disclosed is designed to hold the disclosed cards in a position to permit light readings of a specimen and is applicable to use with specimens other than fabric materials. The holding plate design can be modified for use with various spectrophotometer configurations or other machines. The novel features of the holding plate lie in the ability to remove and replace the card and obtain accurate readings without the necessity of removing the holding plate. Other uses for the holding card, holding plate and tracking system will be obvious to those skilled in the art when read in combination with this disclosure.

What is claimed is:

1. A method of measuring the color of a material against a control specimen to ensure consistent reproduction of said material's color using a holding plate and fabric card combination with a spectrophotometer, said combination having:

a card, said card having a body having a first end, a second end, a first side and a second side, at least of portion of said second side of said second portion being a light absorbing color; a fold line, said fold line being approximately equidistant between said first end and said second end and forming a front section and a back section of substantially equal size; a pair of windows within said body, each of said windows having a center point, said center point being equidistant from said fold line; a fabric recess, said fabric recess encompassing one of said pair of windows; sealing means on said first side of said card, said sealing means maintaining said front section and said back section adjacent one another when folded along said fold line;

a holding plate having a first end and a second end forming a length; a front surface and a back surface forming a width; a recessed area, said recessed area extending from said front surface for a predetermined distance into said width to form a back wall and dimensioned to receive fabric industry color tiles; a window, said window extending through said width, said window being positioned to align with said spectrophotometer's window; a lip, said lip extending around at least a portion of the perimeter of said recessed area and being spaced from said back wall; a slot, said slot being open at said holding plate first end and having a width and length greater than said recessed area, said slot being open to said recessed area, comprising the steps of:
a. choosing a specific, repeated pattern within said fabric;
b. centering said specific, repeated pattern over a die cutter;
c. cutting said fabric to create a control specimen;
d. repeating steps a and b;
e. cutting said fabric to create a customer specimen;
f. removing fabric adhesive covers from submit holding card;
g. centering said control specimen over holding card window;
h. placing said control specimen onto said fabric area adhesive;
i. removing permanent adhesive covers;
j. folding said holding card at said fold line;
k. sealing said permanent adhesives onto themselves to maintain said holding card in a closed position;
l. placing said holding card into said holding plate;
m. taking a color reading of said specimen;
n. storing the color reading of said specimen;
o. printing color readings for said specimen and affixing said readings to said holding card;
p. repeating steps c–o for each specimen;
q. retaining said control specimen for reference;
r. forwarding said customer specimen to said customer for future ordering;

wherein said color reading affixed to said card reflects a numeric value assigned to said fabric swatch by said spectrophotometer enabling subsequent fabric runs to be compared and matched to said control specimen, said customer specimen enabling said customer to compare new and current fabric colors to said customer specimen for reorder and verification of ordered color.

2. The method of claim 1 wherein said cards containing said control specimens and said customer specimens are stored in sheets within a book, said sheets having pockets dimensioned to receive said cards and protecting said fabric swatches from UV rays.

* * * * *